United States Patent [19]

Bacehowski et al.

[11] Patent Number: 4,459,169

[45] Date of Patent: Jul. 10, 1984

[54] ROTATABLE BOWL ASSEMBLY FOR CENTRIFUGAL PROCESSING APPARATUS HAVING A BONDED AND PREWOUND UMBILICAL SYSTEM

[75] Inventors: David V. Bacehowski, Wildwood; Ronald Bucheger, Arlington Hgts, both of Ill.

[73] Assignee: Baxter Travenol Laboratories, Inc., Deerfield, Ill.

[21] Appl. No.: 478,113

[22] Filed: Mar. 23, 1983

Related U.S. Application Data

[62] Division of Ser. No. 244,398, Mar. 16, 1981.

[51] Int. Cl.$^3$ .................. B31F 23/10; B32B 31/00; C09J 5/00; C09J 5/02
[52] U.S. Cl. ............................. 156/221; 138/111; 138/125; 138/126; 138/129; 138/141; 138/150; 156/83; 156/196; 156/296; 156/305; 156/308.6; 494/17; 494/18; 494/42
[58] Field of Search .................. 494/17, 18, 35, 42, 494/43, 85; 138/111, 125, 126, 129, 141, 150; 210/927; 156/166, 143, 308.6, 296, 83, 221, 196, 305, 425; 8/130.1; 428/36, 364

[56] References Cited

U.S. PATENT DOCUMENTS

| | | | |
|---|---|---|---|
| 607,932 | 7/1898 | Husham | 138/111 |
| 2,079,133 | 5/1937 | Taylor | 8/130.1 |
| 2,768,843 | 10/1956 | Zeilman | 285/137 R |
| 3,268,312 | 8/1966 | Grant | 65/3.44 |
| 3,580,764 | 5/1971 | Gerlach et al. | 156/296 |
| 3,885,735 | 5/1975 | Westbert | 494/27 |
| 3,951,174 | 4/1976 | Conant | 138/150 |
| 3,986,442 | 10/1976 | Khoja et al. | 74/797 |
| 4,056,224 | 11/1977 | Lolachi | 494/18 |
| 4,082,217 | 4/1978 | Westberg | 494/15 |
| 4,092,997 | 6/1978 | Hansen | 137/351 |
| 4,109,852 | 8/1978 | Brown et al. | 494/18 |
| 4,113,173 | 9/1978 | Lolachi | |
| 4,146,172 | 3/1979 | Cullis et al. | 494/17 |
| 4,164,318 | 4/1979 | Boggs | 494/18 |
| 4,228,009 | 10/1980 | Ito | 494/85 |
| 4,389,206 | 6/1983 | Bacehowski et al. | 494/42 |
| 4,389,207 | 6/1983 | Bacehowski et al. | 494/42 |

FOREIGN PATENT DOCUMENTS 988480  5/1976  Canada .

OTHER PUBLICATIONS

Excerpt from *Science*, vol., (Sep., 1975) "New Flow--Through Centrifuge Without Rotating Seals Applied to Plasmapheresis," pp. 999-1000.

*Primary Examiner*—Edward C. Kimlin
*Assistant Examiner*—Ramon R. Hoch
*Attorney, Agent, or Firm*—Paul C. Flattery; Daniel D. Ryan

[57] ABSTRACT

A rotatable processing bowl assembly adapted for mounting in a centrifuge includes an umbilical tubing system formed of a plurality of individual flexible tubes each of which communicates with the processing bowl. Each tube has an exterior wall and includes a first portion extending adjacently from the bowl and a second portion which is spaced from the bowl. The exterior walls of the tubes are bonded together along their first portions so that the joined exterior walls collectively define the outer periphery of the tubing system along the first portions of the tubes. Preferably, the tubes are also wound to form a predetermined helical pattern along their first portions. This arrangement enhances the tubing system's durability and resistance to fatigue along the bonded together first portions, particularly at higher rotational speeds, and permits direct, facile connection of the free and unattached second portions with external apparatus.

2 Claims, 4 Drawing Figures

ROTATABLE BOWL ASSEMBLY FOR CENTRIFUGAL PROCESSING APPARATUS HAVING A BONDED AND PREWOUND UMBILICAL SYSTEM

This is a division of application Ser. No. 244,398, filed Mar. 16, 1981.

FIELD OF THE INVENTION

The invention generally relates to centrifugal processing apparatus. More particularly, the invention relates to centrifugal processing apparatus which employ umbilical tubing which is rotated with respect to a stationary base.

DESCRIPTION OF THE PRIOR ART

Many uses for centrifugal processing apparatus are known. One important field of use, for example, is the separation of blood or other biological liquids.

In this field of use, attention is directed to the following U.S. Pat. Nos., all of which concern centrifugal blood separation processing equipment which utilize a flexible, multiple lumen umbilical cord to establish fluid communication between a rotating bowl and stationary reservoirs or containers:

Adams, 3,586,413, June 22, 1971
Westbert, 3,885,735, May 27, 1975
Khoja, 3,986,442, Oct. 19, 1976
Lolachi, 4,056,224, Nov. 1, 1977
Westberg, 4,082,217, Apr. 4, 1978
Brown, 4,108,353, Aug. 22, 1978
Brown et al., 4,109,852, Aug. 19, 1978
Brown et al., 4,109,855, Aug. 29, 1978
Boggs et al., 4,111,356, Sept. 5, 1978
Khoja, 4,113,173, Sept. 12, 1978
Khoja et al., 4,127,231, Nov. 28, 1978
Khoja et al., 4,132,349, Nov. 11, 1977
Cullis et al., 4,151,844, Nov. 11, 1977
Boggs, 4,164,318, Aug. 14, 1979

In the Westberg and Westbert patents, a torsionally rigid wire extends through the core of the umbilical cord to reduce twisting of the cord during rotation of the bowl.

In all of the remaining patents, the umbilical cord is itself caused to rotate about the rotational axis of the bowl in a path axially outwardly of the bowl and at one-half the rotational speed of the bowl. This principle of operation is disclosed in the above-cited Adams patent and prevents twisting of the cord during centrifugation. Among the many advantages of this method of operation is the elimination of the use of rotating seals, which are expensive and add to the possibility of contamination of the fluid being processed.

In such arrangements, centrifugal forces acting upon the rotating umbilical cord can adversely effect the durability and structural integrity of the cord. These forces are particularly pronounced at progressively higher rotational speeds, as well as in those portions of the cord which are adjacent to the rotatable processing bowl.

In the past, various approaches have been utilized to reduce the stresses generated during centrifugation. For example, utilizing an umbilical cord of coextruded multi-lumen construction, instead of multiple, independent tubing, can enhance the cord's overall durability. Furthermore, to further enhance the cord's resistance to centrifugal fatigue, a flexible strain relief sheath has been employed in combination with the multi-lumen umbilical cord (as in Brown et al, U.S. Pat. No. 4,109,852; Brown et al, U.S. Pat. No. 4,109,855; and Boggs U.S. Pat. No. 4,164,318), or the multi-lumen umbilical cord itself has been stretched to exhibit a reduced diameter, and thus a reduced rotational mass, in those portions where relatively larger centrifugal loads are encountered (as in Boggs U.S. Pat. No. 4,164,318).

In this regard, attention is also directed to pending U.S. Application Ser. No. 195,445, filed Oct. 9, 1980, now abandoned, as well as to pending U.S. Application Ser. No. 194,205, filed Oct. 6, 1980. Both of these applications are assigned to the assignee of the present invention and generally address the same area of concern.

SUMMARY OF THE INVENTION

One of the principal objects of the invention is to provide flexible umbilical tubing which exhibits durability and resistance to fatigue, particularly at higher rotational speeds, without the use of relatively expensive co-extruded multiple lumen tubing, outer protective sleeves or sheaths, interior stiffeners, and the like.

It is another one of the principal objects of the invention to provide a rotatable processing bowl assembly having a durable umbilical tubing arrangement which can be manufactured in a straightforward, simplified process.

To achieve these and other objects, an umbilical tubing system is provided which is adapted for use with a rotatable processing bowl adapted for mounting in a centrifuge. The tubing system includes a plurality of individual, independently formed flexible tubes. The individual tubes are adapted to communicate with the bowl at various different radial locations to introduce a material for centrifugation into the bowl and to remove various centrifugally separated components of the material from the bowl.

In accordance with this invention, portions of the umbilical tubes which extend adjacently from the bowl are solvent bonded together, preferably in a helically wound relationship, to enhance the overall durability and operational performance of the tubes in the areas where maximum centrifugal forces are normally encountered.

Other portions of the umbilical tubes, which integrally extend from the bonded together portions but which are positioned farther from the processing bowl than the bonded together portions, and thus away from the areas of maximum stress, are left free of bonding to each other to facilitate their connection with a patient and various blood component collection containers.

The invention provides a umbilical tubing system which exhibits resistance to fatigue during centrifugation without the use of a relatively complex cord of multiple lumen construction, a protective sleeve or sheath, interior stiffeners, or the like, and which also permits direct, facile connection with external apparatus.

The invention also provides a method of manufacturing the umbilical tubing system as above generally described.

Other features and advantages of the invention will be pointed out, or will be apparent from, the specification and claims, as will obvious modifications of the embodiment shown in the drawings.

DESCRIPTION OF THE PREFERRED EMBODIMENT

Figure 1:
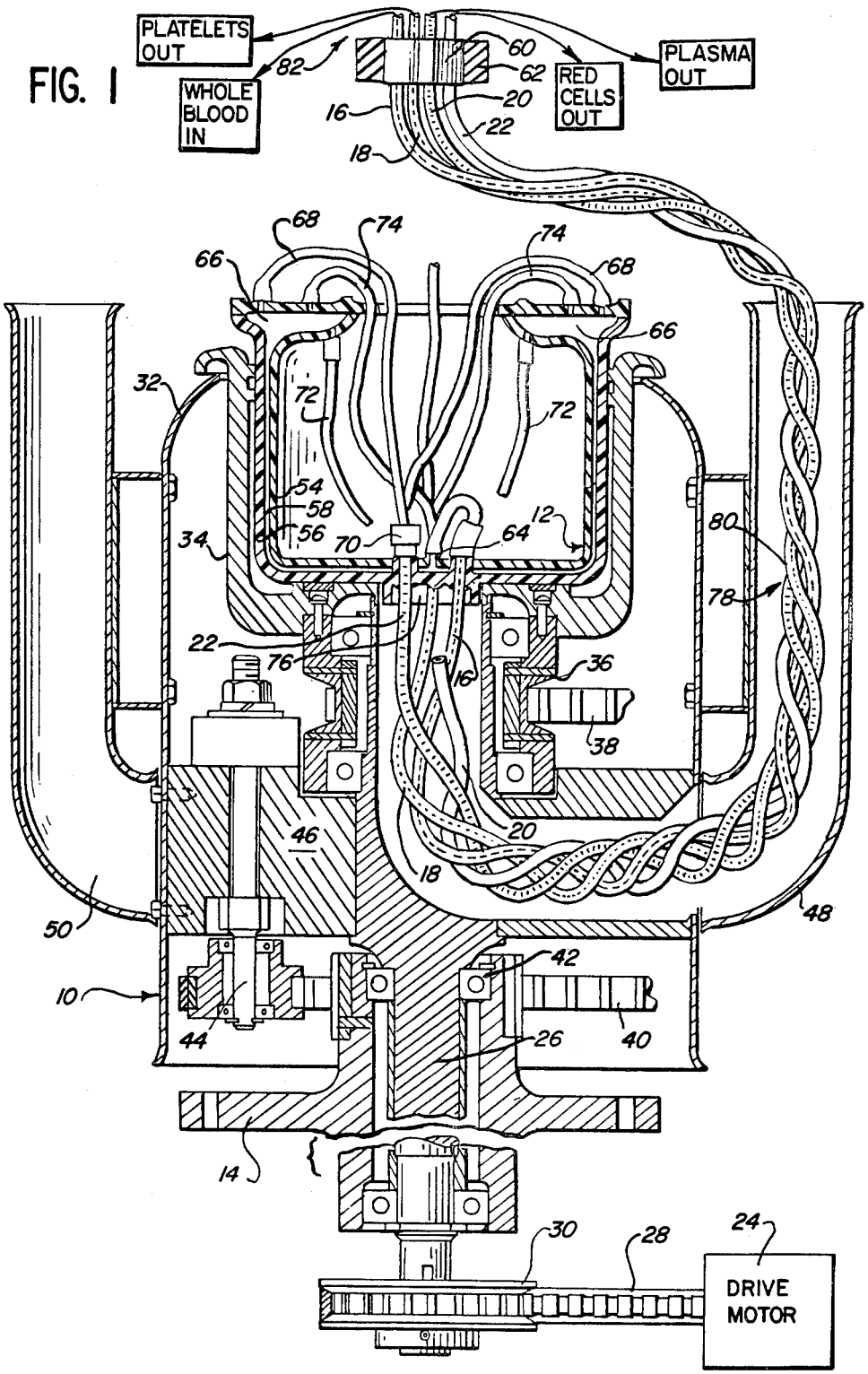
FIG. 1 is a sectional view of a centrifugal processing apparatus containing a rotatable processing bowl having an associated umbilical tube system which embodies various of the features of the invention.

A centrifugal processing apparatus 10 which, in the illustrated embodiment, takes the form of a blood centrifuge, is shown in FIG. 1. The apparatus 10 is positioned on a generally stationary base 14 and carries a rotatable processing bowl 12. A plurality of individual, independently formed, and flexible umbilical tubes 16, 18, 20, 22 communicates with one end of the processing bowl 12 in a manner which will be described in greater detail later herein.

Preferably, the bowl 12 and its associated umbilical tubes 16, 18, 20, 22 together constitute a removable and disposable assembly which is replaced after each separate blood processing procedure.

The apparatus 10 may be driven in accordance with various generally known principles. In the illustrated embodiment (and still referring to FIG. 1), the apparatus 10 encorporates a drive system which utilizes the heretofore-described principle of operation of the Adams patent (U.S. Pat. No. 3,586,413) and is similar to that described in the previously described U.S. Pat. No. 4,132,349.

More particularly, in the illustrated embodiment, a suitable drive motor 24 is operatively connected with a drive shaft 26, such as by a belt 28 and drive pulley 30 arrangement, to thereby rotate the drive shaft 26. The drive shaft 26, in turn, carries a receptacle 34 for common rotation therewith. The processing bowl 12 can be removably positioned within the receptacle 34 in the manner shown in FIG. 1 for common rotation therewith.

An outer housing 32 is supported for rotation about and relative to the drive shaft 26. More particularly, a gear reducer bearing 36 rotates with the drive shaft 26 and is operatively connected by means of a belt 38 with a conventional gear system (which is not shown). Another belt 40 is operatively connected with the same gear system and with another rotational bearing 42 which rotates the outer housing 32 by means of a rotating arm 44 and a retention member 46. The gear system is designed to rotate the outer housing 32 at one-half the rotational velocity of the shaft 26 and, thus, at one-half the rotational velocity of the bowl 12.

J-shaped tubings 48 and 50 are fixed to the outer housing 32 axially outwardly of the axis of rotation. One J-shaped tubing 48 is positioned to receive the umbilical tubings 16 through 22 which extend adjacently from the bowl 12. The other J-shaped tubing 50 acts as a counterbalance.

The rotatable processing bowl 12 includes radially spaced inner and outer walls, respectively 54 and 56, between which a flow passage 58 is formed. The individual tubes 16 through 22 communicate with different radial locations of the passage 58 and extend axially outwardly from the bowl 12, through the J-shaped tubing 48, and thence upwardly through a stationary plug member 60 positioned by a retention bracket 62 directly above the rotational axis of the bowl 12.

The plug member 60 acts as a stationary base for the tubes 16 through 22 during centrifugation, and rotation of the housing 32 carries the portions of the umbilical tubes 16 through 22 extending through the J-shape tubing 48 in a circular path about the rotational axis of the shaft 26 at one-half the speed of rotation of the shaft 26.

While the tubes 16 through 22 may be variously constructed, they are preferably constructed of a polyvinyl chloride plastic material as is generally described in co-pending Application Number 195,445, heretofore cited.

Similarly, the total number of tubes 16 through 22 utilized may vary according to the particular use to which the apparatus 10 is put. However, in the illustrated embodiment, in which use of the apparatus 10 as a blood centrifuge is contemplated, four individual tubes 16 through 22 are utilized.

In such use, whole blood enters the umbilical tube 16, being supplied from a conventional blood bag or directly from the patient. The blood in the umbilical tube 16 enters into the bowl 12 and loops downwardly through a port 64 to enter the flow passage 58. As the bowl 12 is rotated by the apparatus 10, blood migrates through the flow passage 58 upwardly into the enlarged annular chamber 66.

Due to the centrifugal action, the red cells migrate outwardly from the whole blood on a continuous basis and are collected through the radially outermost collection conduits 68. These red cell collection conduits 68, in turn, connect through a multiple connector 70 with the umbilical tube 22, through which red cells are withdrawn from the bowl 12 for reinfusion to the patient or collection and storage.

At the same time, the plasma collects at the radially innermost portions of the annular chamber 66 and is collected through the radially innermost conduits 72. The plasma conduits 72 are all connected together in a multiple manifold connector (not shown, but similar to connector 70) to connect with the umbilical tube 20 for collection in containers which are connected to the free end of tubing 20. Alternatively, the collected plasma may be directly reinfused to the patient.

Meanwhile, a layer of white cells and platelets (commonly called a "buffy-coat") forms between the red cells and the plasma. This layer is collected through the conduits 74 which communicate with the annular chamber 66 at a radial position between the conduits 69 and 72. The conduits 74 connect with the umbilical tube 18 through a multiple manifold chamber 76.

As before mentioned, portions of the individual umbilical tubes 16 through 22 (generally designated as portions 78 in FIG. 1) extend adjacently from the bowl 12 and are carried during centrifugation within the J-shape tubing 48 in a circular path about the rotational axis of the bowl 12. These portions 78, like the material in the bowl 12, are subject to centrifugal forces, which increase in intensity as rotational speeds increase. Portions of the tubes 16 through 22 (generally designated as portions 82 in FIG. 1) which are more remotely spaced from the bowl 12, and in particular, extend outwardly beyond the stationary plug member 60, generally do not participate in the rotary motion and are thus generally not subjected to centrifugal forces of comparable intensities.

When the portions 78 which are subject to centrifugal forces consist of an array of free and unjoined umbilical tubes, each umbilical tube 16 through 22 is observed to react individually to the various centrifugal forces. Affecting the particular individual reaction of each umbilical tube 16 through 22 are such interdependent variables as (1) the overall length of the tube between the bowl 12 and the plug member 60; (2) the overall length of the tube relative to the corresponding overall length of the adjacent tubes (all tubes 16 through 22 should be generally equal in length for most efficient operation); and (3) the orientation of the tube after the operator has positioned the bowl 12 in the apparatus 10.

When a particular operationally desirable relationship exists among these variables, the portions 78 of the umbilical tubes 16 through 22 are observed to mutually wrap themselves into an essentially stable helical configuration in the direction of centrifugal rotation.

However, more often than not, this operationally desirable relationship among the tubes does not develop because, for example, the tubes 16 through 22 are initially misoriented by the operator or become misoriented during centrifugation, or the relative lengths of the tubes are not within the desired range of equality. In this situation, the tubes 16 through 22 may not "set" in the above described configuration during operation of apparatus 10, but rather may continuously twist, wear, and slap in essentially random fashion against each other in response to the centrifugal forces. As a result, overtwisting of an individual umbilical tube can result, thereby causing an occlusion or restriction in that tube; and/or the umbilical tubes can rub or wear against each other or against portions of the J-shaped tubing 48, thereby causing incidences of fatigue; and/or the random contact of the tubes against each other can cause noise. Such random activity of the umbilical tubes 16 through 22 in this situation increases as progressively higher rotational speeds are encountered.

In accordance with the invention, the portions 78 of the individual umbilical tubes 16 through 22 are bonded together to form a single, integrally joined tubing assembly, generally designated 80 in FIG. 1.

The bonded tubing assembly 80 reacts to the forces of centrifugation as a single, integral unit, and not in essentially random fashion as four free and unattached tubes 16 through 22. As a result, centrifugal forces are generally equally distributed along the entire length of the bonded assembly 80, and do not cause isolated incidences of wear and fatigue. The overall durability and integrity of each of the integrally bonded tubes 16 through 22 is improved, particularly at higher centrifugal speeds, and the overall operational efficiency of the umbilical tube assembly 80 is enhanced. Furthermore, since the individual tubes 16, 18, 20 and 22 are no longer free to slap against each other, noise levels during centrifugation can be noticeably decreased.

In the illustrated preferred embodiment, the bonded portions 78 of the tubes 16 through 22 forming the assembly 80 are also permanently prewound together into a helical configuration. The winding serves to increase the bonding area, and thus further strengthen the bond, between the individual tubes 16, 18, 20, and 22. The winding also serves to approximate the essentially stable configuration the tubes, if free and unattached, would seek when the particular operationally desirable relationship existed among them. The overall durability and operational performance of the bonded tubing assembly 80 is thus further enhanced.

Because the portions 82 of the tubes 16 through 22 are not subject to the same centrifugal forces as portions 78, these portions 82 can remain free of bonding to each other and free of the helically wound relationship of portions 78.

Figure 2:
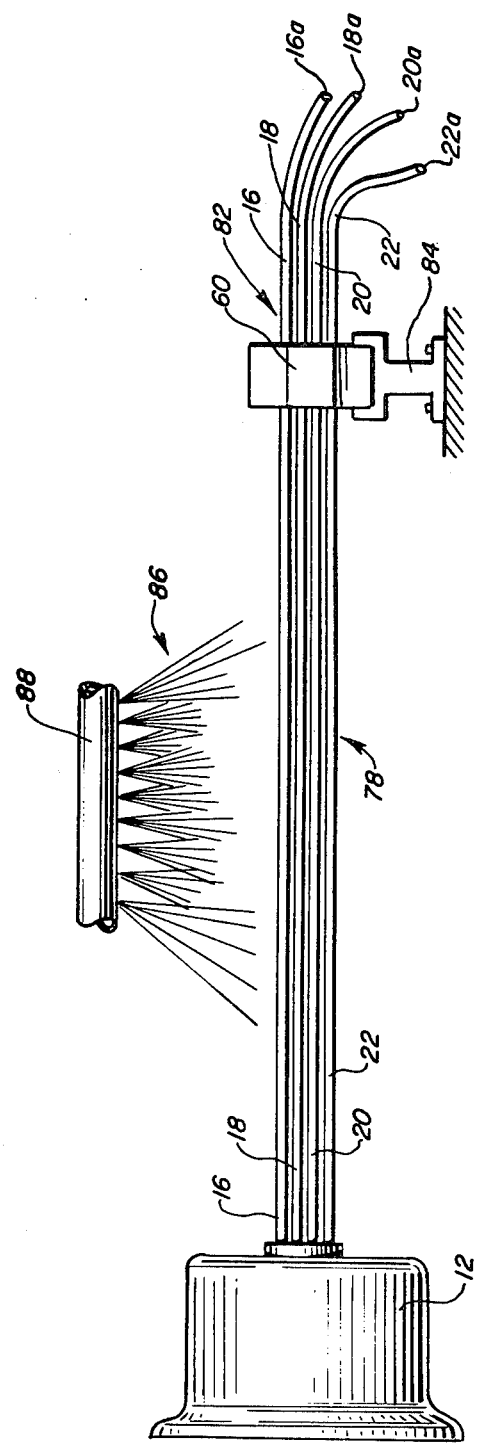
FIG. 2 is a generally downwardly looking view of the processing bowl and umbilical tube system shown in FIG. 1 in the initial stages of being manufactured.
Figure 3:
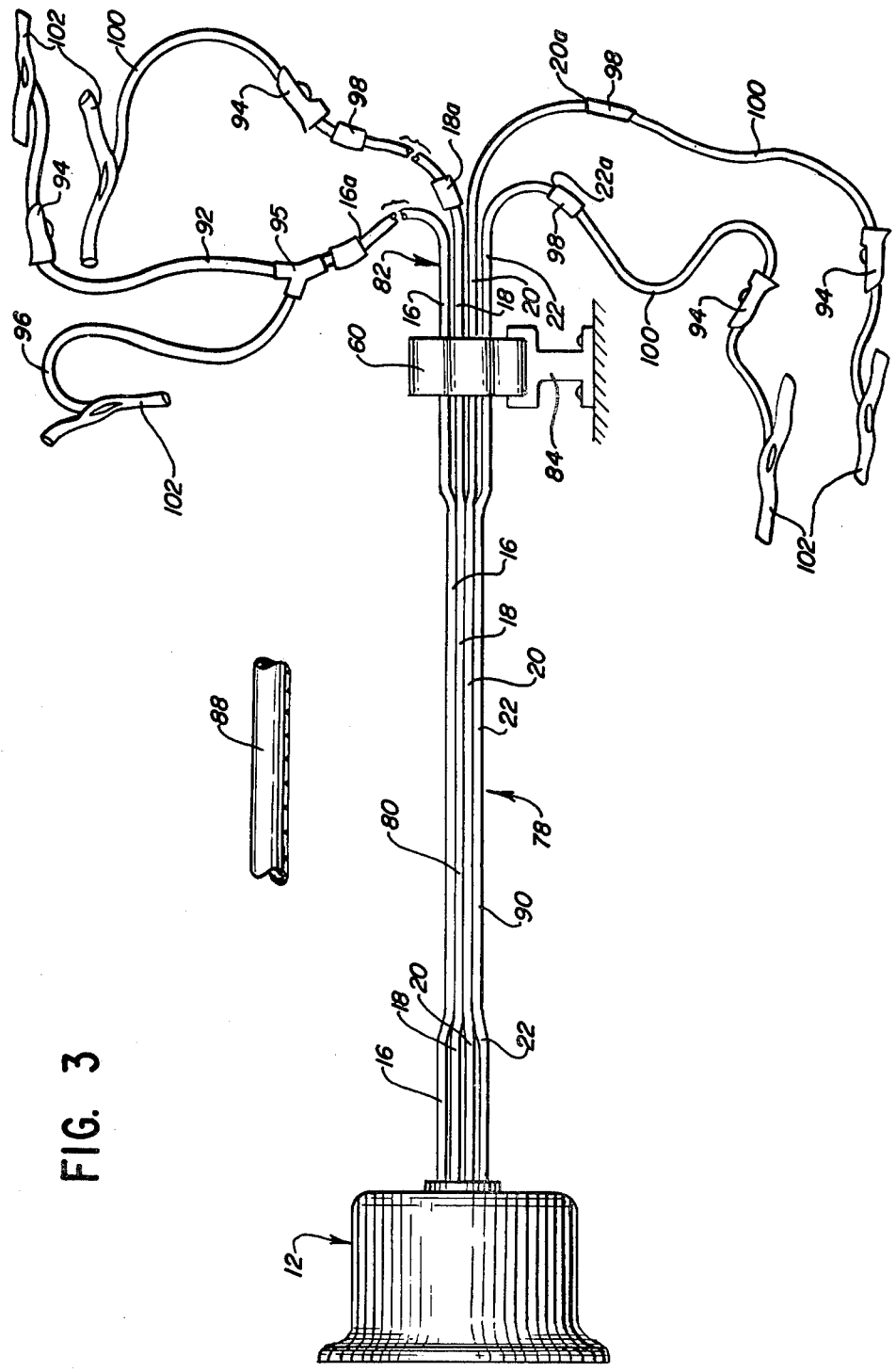
FIG. 3 is a generally downwardly looking view of one embodiment of umbilical tube system in the latter stages of being manufactured, in which a portion of the system has been solvent bonded together.
Figure 4:
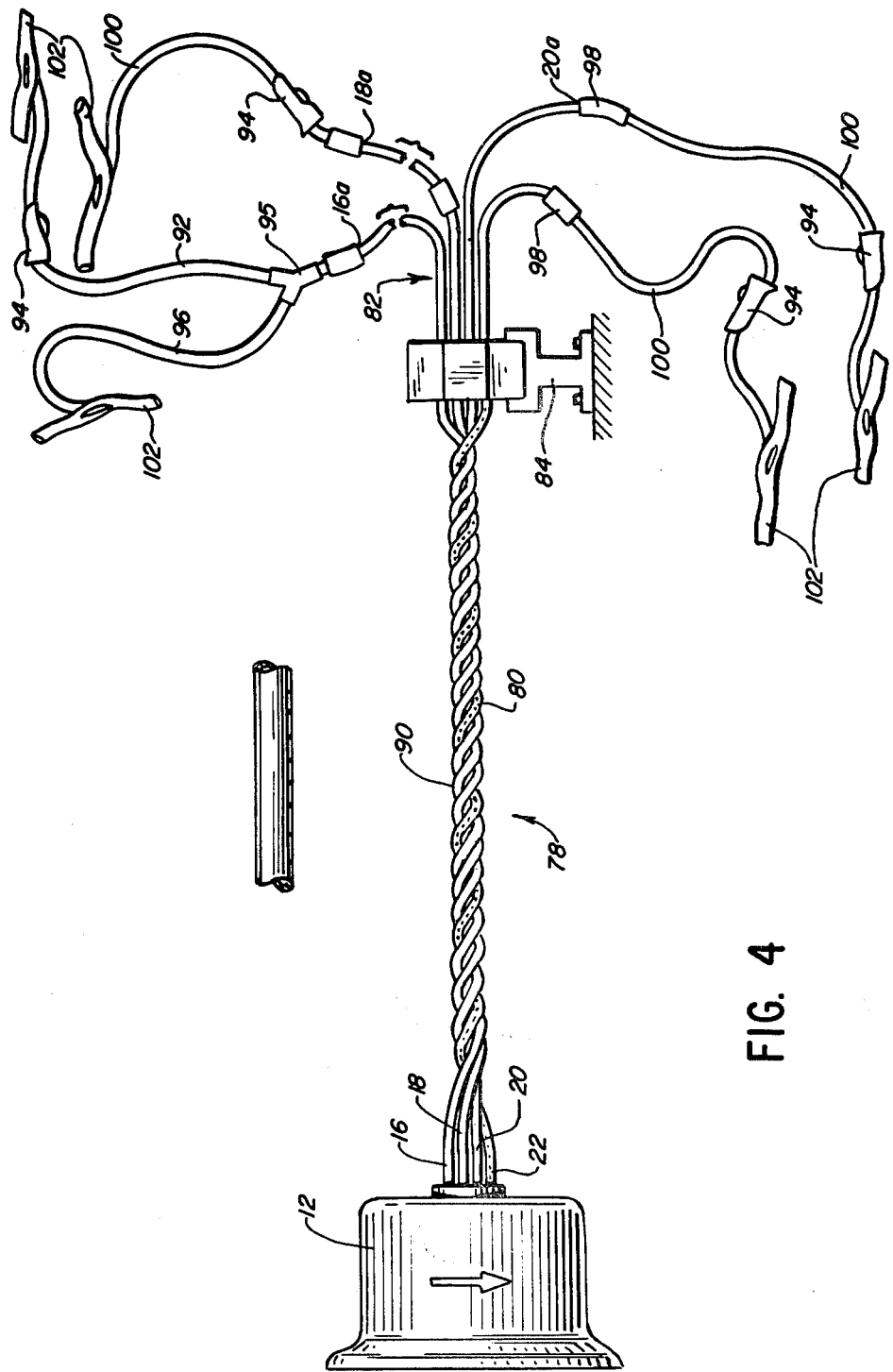
FIG. 4 is a generally downwardly looking view of another embodiment of the umbilical tube system in the latter stages of being manufactured in which a portion of the system has been solvent bonded together in a helically wound relationship.

Reference is now made in particular to FIGS. 2 through 4, and to the method of forming the umbilical tube systems as just described. In this method, the individual lengths of tubing 16 through 22 are attached to the bowl 12 to form the desired communication with the flow passage 58. The plug member 60 is then attached and positioned in a stationary bracket 84.

The bowl 12 is then laterally positioned in a spaced relationship from the bracket 84 and rotationally positioned so as to arrange the umbilical tubes 16 through 22 in a generally taunt and parallel relationship relative to each other, as shown in FIG. 2. A controlled spray of solvent 86 is next directed, such as by use of a series of spray orifices 88, upon the exterior walls of the tubes 16 through 22 along predetermined portions 78.

As heretofore described, these portions 78 correspond to the areas of the tubes which extend where centrifugal forces are normally encountered, and, in particular, those areas which are to extend axially outwardly from the bowl 12 through the J-shape tubing 48 when the apparatus 10 is in operation.

Typically, a solvent such as cyclohexanone may be used, particularly when the tubes 16 through 22 are made of polyvinyl chloride plastic. However, any other appropriate solvent may be used, depending upon the particular plastic material from which the tubes are made.

After the exterior walls of the tubes 16 through 22 have been thoroughly wetted with the solvent 86 along portions 78, the exterior walls may be brought together, as shown in FIG. 3, keeping the same generally parallel arrangement of the tubes shown in FIG. 1, and thereafter held stationary until the solvent 86 has evaporated. The exterior walls of the umbilical tubes 16 through 22 are thus bonded together along portions 78 to form the heretofore described integrally joined tubing assembly 80, with the joined exterior walls collectively defining the outer periphery 90 of the assembly 80.

However, in accordance with the preferred embodiment, and as is shown in FIG. 4, after the exterior walls have been thoroughly wetted with the solvent 86 along portions 78, the bowl 12 is rotated in the direction of intended rotation of the centrifuge 10 (which is shown by arrows in FIG. 4 to be clockwise). The wetted exterior walls of the umbilical tubes 16 through 22 are thus brought together in the helical relationship shown in FIGS. 1 and 4, and held stationary in this relationship until the solvent 86 has evaporated. The exterior walls are now bonded together to maintain the tubing in the assembly 80 in the helical pattern, with the joined exterior walls collectively defining the outer periphery 90 of the assembly 80.

There is an advisable range of winding which should be undertaken to form the helically wound relationship of the assembly 80. A "loose" relationship resulting from not enough bowl rotation and too few helical loops does not generally enhance the bonding area between the tubes, whereas a "tight" relationship resulting from too much rotation and too many helical loops can lead to restrictions and occlusions of the tubes.

The particular advisable range varies, for the most part, according to the maximum outer diameter of the tubes employed. In the illustrated embodiment, in which the tubes carry various parenteral fluids and a maximum outer diameter of approximately 0.25 inches for each tube is normally encountered, the formation of between two to eight helical loops per each wound foot of tubing is advisable.

As is shown in FIGS. 2, 3, and 4, the portions 82 of the umbilical tubes 16 through 22 which integrally extend from the bonded together portions 78 include end portions, respectively 16a, 18a, 20a and 22a, which are free of bonding to each other. In the embodiment shown in FIG. 4, the end portions 16a through 22a are also free of the helically wound relationship of the portions 78.

The free tube end portions 16a through 22a are also freely movable relative to each other and can be readily connected to various external apparatus associated with blood processing, as well as to the patient.

While the specific nature of the attachments varies according to the particular objectives of the blood processing operation, in FIGS. 3 and 4, free tube end portion 16a, which is an integral extension of the tube 16 through which whole blood is carried into the bowl 12, carries a Y-connector member 95, to which a branch line 92 which may be connected. The branch line 92, in turn, may be connected to a conventional inlet set (not shown) attached to the patient and a source of sterile saline solution. In-line roller clamp 94 is provided to control the flow of whole blood from the patient through the tube 16.

A branch line 96 is also connected to the Y-connector member 95. The branch line 96 is adapted for connection with a suitable high pressure monitoring system (not shown) associated with the apparatus 10.

Free tube end portion 18a, which is an integral extension of the umbilical tube 18 through which the "buffy-coat" layer of white cells and platelets is removed from the bowl 12, may accordingly be used for platelet and white cell collection and may be attached to a suitable receptacle (not shown) for this purpose. A connector member 98 may be utilized to connect the free end portion 16a to a collection tube 100 having a smaller, equal, or larger bore diameter, as desired. An in-line roller clamp 94 may also be provided to control the flow.

Free tube end portion 20a, which is an integral extension of the umbilical tube 20 through which the plasma is removed from the bowl 12, may be used for plasma collection and may be attached to a suitable receptacle (not shown) for this purpose. As with tube end portion 18a, a connector member 98 may be utilized, if desired, to connect the free end portion 20a to a collection tube 100 of the same or different bore size, and an in-line roller clamp 94 employed to control fluid flow.

Lastly, free tube end portion 22a, which is an integral extension of the umbilical tube 22 carrying red blood cells from the bowl 12, may be used for red blood cell collection and attached to a receptacle (not shown) for this purpose. Alternately, the free tube end portion 22a may be connected with the patient, to reinfuse the red blood cells. As before, a connector member 98 and collection tube 100 arrangement and a roller clamp 94 may be employed, if desired.

The terminal ends of the branch lines 92 and 96 and collection tubes 100 are preferably provided with tab members 102 to maintain sterility until actual use.

The umbilical tube system as just described exhibits durability and resistance to fatigue without employing relatively expensive coextruded multiple lumen tubing, outer protective sleeves or sheaths, interior stiffeners, and the like. The tube system also permits direct and facile connection with external apparatus. Furthermore, the system lends itself to a straightforward, simplified manufacturing process.

Although the invention has been described strictly in the context of centrifugal blood processing operations, it should be appreciated that the invention is applicable for use in diverse environments where centrifugal forces are encountered.

Furthermore, it should be appreciated that various changes and modifications can be made without departing from the spirit of the invention or from the scope of the appended claims.

We claim:

1. A method of manufacturing a rotatable processing bowl assembly having a bowl and a plurality of individual, flexible umbilical tubes establishing communication with the bowl, said method comprising the steps of:
    (a) securing a section of each of the flexible umbilical tubes, creating a first portion of the tubes extending between the secured section and the bowl and a second portion extending from the secured section away from the first portion;
    (b) coating the first portion of the flexible umbilical tubes with a solvent for the material of the umbilical tubes;
    (c) rotating the bowl about its axis of rotation a predetermined number of turns relative to the second portion to form a helically wound pattern in the first portion; and
    (d) retaining the first portion in the helically wound pattern until said solvent has dried, to cause the umbilical tubes of said first portion to be bonded together in the helically wound pattern and the umbilical tubes of the second portion to be free and unattached to each other.

2. A method according to claim 1 wherein said rotating step (c) includes rotating the bowl so as to form between two to eight loops per wound foot of tubing in the first section.

* * * * *